United States Patent [19]

Shaner

[11] Patent Number: 5,356,789
[45] Date of Patent: Oct. 18, 1994

[54] METHODS FOR DETECTING ACETOHYDROXYACID SYNTHASE INHIBITORS

[75] Inventor: Dale L. Shaner, Lawrenceville, N.J.

[73] Assignee: American Cyanamid Company, Wayne, N.J.

[21] Appl. No.: 68,458

[22] Filed: May 28, 1993

[51] Int. Cl.$^5$ .................. C12Q 1/26; A01N 27/00; A01N 35/06; A01N 57/02

[52] U.S. Cl. .................. 435/25; 424/9; 435/189; 436/128; 436/129; 436/131; 504/116; 504/130; 504/148; 504/225; 504/273

[58] Field of Search .................. 435/25, 69.2, 189; 424/94.4, 9; 504/116, 130, 148, 225, 273; 436/128, 129, 131

[56] References Cited

PUBLICATIONS

Shaner et al. "Interaction of Imidazolinones w/ Plant Acetohydroxy Acid Synthase: Evidence for in vivo Binding and Competition w/ Sulfoneturon Methyl" J. Agric Food Chem. 38: 1990, pp. 1279–1282.

Chundunu et al "Mechanism of Ketol Acid Reductoisomerase-and Steady State Analysis & Metal Ion Requirement" Biochemistry 28: 486–493, 1989.

D. L. Shaner, et al, Plant Physiol., 76, pp. 545–546 (1984).

S. Epelbaum, et al, Analytical Biochemistry, 191, pp. 96–99 (1990).

A. Aulabaugh & J. V. Schloss, Biochemistry, 29, pp. 2824–2830 (1990).

B. C. Gerwick, et al, Pestic. Sci., 29, pp. 357–364 (1990).

A. Schulz, et al, FEBS Letters, 238 (2), pp. 375–378.

D. L. Shaner, Herbicide Resistance in Weeds and Crops, ed. J. C. Caseley, G. W. Cussans and R. K. Atkin (Oxford: Butterworth-Heinemann, 1991), 187–198.

J. V. Schloss & A. Aulabaugh, Biosynthesis of Branched Chain Amino Acids, ed. Z. Barak, D. M. Chipman & J. V. Schloss (New York: VCH Publishers, 1990), 329–356.

J. V. Schloss, Flavins and Flavoproteins, ed. R. C. Bray, P. C. Engel and S. G. Mayhew (Berlin: Walter de Gruyter, 1984), 737–740.

J. deCastro & C. D. Youmans, Proc. West. Soc. Weed Sci., 43, pp. 79–80 (1990).

B. J. Miflin, Arch. Biochem. Biophys., 146, pp. 542–550 (1971).

W. W. Westerfeld, J. Biol. Chem., 161, pp. 495–502 (1945).

G. Mourad and J. King, Planta, 188, pp. 491–497 (1992).

Primary Examiner—Jeffrey E. Russel
Assistant Examiner—Nancy J. Gromet
Attorney, Agent, or Firm—M. P. Morris

[57] ABSTRACT

The invention provides a method for determining whether a compound inhibits acetohydroxyacid synthase. The invention further provides a method for determining whether a plant is resistant to an acetohydroxyacid synthase inhibiting compound.

19 Claims, No Drawings

METHODS FOR DETECTING ACETOHYDROXYACID SYNTHASE INHIBITORS

BACKGROUND OF THE INVENTION

The pathway leading to the biosynthesis of branched chain amino acids (valine, leucine and isoleucine) is vital to the survival of plants. This pathway, and the enzymes promoting it, is vulnerable to several classes of highly potent herbicides including imidazolinones, sulfonylureas, sulfonamides and pyrimidyloxybenzoates. Such herbicides act by inhibiting acetohydroxyacid synthase (AHAS), the first enzyme functioning in the pathway.

Recently, weed populations have been discovered which are resistant to AHAS-inhibiting herbicides (D. L. Shaner, *Herbicide Resistance in Weeds and Crops*, ed. J. C. Caseley, G. W. Cussans and R. K. Atkin (Oxford: Butterworth-Heinemann, 1991), 187–198). These resistant biotypes contain an altered AHAS enzyme which is no longer inhibited by these herbicides. Once such a resistant weed population has developed, the weed management program has to be changed to prevent the propagation of the resistant weed. Therefore, a method to rapidly determine if a weed population has developed resistance to an AHAS-inhibiting herbicide would have great utility and would permit the agriculturalist to adapt his weed management program to control the resistant weed more effectively.

Because several classes of AHAS inhibiting compounds are highly potent herbicides, there is an ongoing search to discover new and more effective AHAS inhibitors. To identify these new inhibitors, assays are used to measure the extent of AHAS inhibition caused by the compounds' use. However, the assays currently employed are often arduous, expensive and/or time-consuming.

It is an object of the present invention to provide a method for determining whether a compound inhibits acetohydroxyacid synthase.

It is also an object of the present invention to provide a method for determining whether a plant is resistant to an acetohydroxyacid synthase inhibitor.

These and other objects of the present invention will become more apparent from the detailed description thereof set forth below.

SUMMARY OF THE INVENTION

The present invention relates to a method for determining whether a compound inhibits acetohydroxyacid synthase (AHAS). In particular, the present invention relates to a method for determining whether a compound inhibits the AHAS enzyme by detecting the presence of and measuring the quantity of its condensation products in a biological system.

The present invention also relates to a novel in vivo method for determining whether a plant is resistant to an AHAS inhibitor. In particular, the present invention relates to a method for determining whether a plant is AHAS-inhibitor resistant by detecting the presence of and measuring the quantity of its condensation products in the biological system and comparing the results to a predetermined standard.

DETAILED DESCRIPTION OF THE INVENTION

Weeds cause tremendous global economic losses by reducing crop yields and lowering crop quality. Several classes of highly potent herbicides effectively control weeds by inhibiting AHAS. Therefore, there is an ongoing search to discover new and more effective AHAS inhibitors. To identify these new inhibitors, assays can be used to measure the products of AHAS activity. However, the assays currently employed are often arduous, expensive and/or time-consuming.

New herbicides have been discovered which inhibit ketol-acid reductoisomerase (KARI), the enzyme which immediately follows AHAS in the branched chain amino acid pathway (J. V. Schloss and A. Aulabaugh, *Biosynthesis of Branched Chain Amino Acids*, ed. Z. Barak, D. M. Chipman and J. V. Schloss (New York: VCH Publishers, 1990), 329–356). Plants treated with these herbicides accumulate acetolactate and acetohydroxybutyrate (AL/AHB), the condensation products of AHAS. The amount of AL/AHB present in the plants can then be measured to determine the extent of inhibition.

Advantageously, the present invention provides a rapid and quantitative method for determining whether a compound inhibits AHAS. The method comprises treating an AHAS inhibitor-susceptible plant or plant part with a biologically active compound and an effective amount of a KARI inhibitor; treating the AHAS inhibitor-susceptible plant or plant part with the KARI inhibitor alone; and measuring the amount of AL and AHB present in the treated plants or plant parts to determine if the amount of AL and AHB present in the plant or plant part treated with the biologically active compound and the KARI inhibitor is less than the amount of AL and AHB present in the plant or plant part treated with the KARI inhibitor alone. Such a result is characteristic of an AHAS inhibiting compound.

Advantageously, the present invention also provides a rapid and quantitative method for determining whether a plant is resistant to an AHAS inhibitor. This method comprises treating a plant or a part of the plant with an effective amount of an AHAS inhibitor and an effective amount of a KARI inhibitor; treating the plant or plant part with an effective amount of the KARI inhibitor alone; and measuring the amount of AL and AHB present in the treated plants or plant parts to determine if the amount of AL and AHB present in the plant or plant part treated with the AHAS inhibitor and the KARI inhibitor correlates with a predetermined AHAS-inhibitor resistance standard. For example, where an effective amount of an AHAS inhibitor and an effective amount of a KARI inhibitor produce a result of at least about 15% of the amount of AL and AHB present in the plant or plant part treated with the KARI inhibitor alone, the plant is essentially AHAS inhibitor resistant. It has been discovered that heterozygous resistant plants treated with an AHAS inhibitor and a KARI inhibitor have about 15% to 50% of the amount of AL and AHB present in the KARI inhibitor-treated plants, and homozygous resistant plants treated with an AHAS inhibitor and a KARI inhibitor have more than 50% of the amount of AL and AHB present in the KARI inhibitor treated plants.

Advantageously, the present invention may be used to determine if weeds are resistant to AHAS inhibitors. Because of the rapidity of the invention methods, critical decisions can be made on how to treat uncontrolled weeds after AHAS inhibitor applications.

Beneficially, the methods of the present invention can be used in the field or laboratory with minimal equipment. And the methods of this invention are more economical and significantly less time-consuming than the enzyme extraction and green house spray procedures currently employed.

KARI inhibitors which are suitable for use in the methods of the present invention include (dimethylphosphinyl)glycolic acid; 2-(dimethylphosphinoyl)-2-hydroxyacetic acid; sodium N-hydroxy-N-alkyloxamates and sodium N-hydroxy-N-aralkyloxamates. For the N-hydroxy-N-alkyloxamates, the alkyl group is preferably $C_1$–$C_6$ alkyl or $C_3$–$C_7$ cycloalkyl, most preferably isopropyl. A preferred aralkyl group is benzyl.

AHAS inhibitors which are suitable for use in the method used to detect resistance include a) imidazolinone inhibitors such as
5-ethyl-2-(4-isopropyl-4-methyl-5-oxo-2-imidazolin-2-yl)nicotinic acid (imazethapyr);
2-(4-isopropyl-4-methyl-5-oxo-2-imidazolin-2-yl)-3-quinolinecarboxylic acid (imazaquin);
isopropylammonium 2-(4-isopropyl-4-methyl-5-oxo-2-imidazolin-2-yl)nicotinate (imazapyr);
methyl 2-(4-isopropyl-4-methyl-5-oxo-2-imidazolin-2-yl)nicotinate; and
2-(4-isopropyl-4-methyl-5-oxo-2-imidazolin-2-yl)-5-methylnicotinic acid;

b) sulfonylurea inhibitors such as
1-(2-chlorophenylsulfonyl)-3-(4-methoxy-6-methyl-1,3,5-triazin-2-yl)urea (chlorsulfuron);
methyl 2-[3-(4,6-dimethylpyrimidin-2-yl)ureidosulfonyl]benzoate (sulfometuron-methyl); and
methyl o-{{3-[4,6-bis(difluoromethoxy)-2-pyrimidinyl]ureido}sulfonyl}benzoate;

c) sulfonamide inhibitors such as
N-(2,6-difluorophenyl)-5-methyl-1,2,4-triazolo[1,5-a]pyrimidine-2-sulfonamide (flumetsulam); and
N-(2,6-dichlorophenyl)-5-methyl-1,2,4-triazolo[1,5-a]pyrimidine-2-sulfonamide; and d) pyrimidyloxybenzoate inhibitors such as
o-[(4,6-dimethoxy-2-pyrimidinyl)oxy]benzoic acid.

Plant species suitable for use in the methods of the present invention include monocotyledonous plant species such as Johnsongrass, blackgrass and corn, and dicotyledonous plant species such as pigweed, morning glory, chickweed, sunflower, tobacco and lima bean. Plant parts suitable for use in the methods of the invention include young rapidly growing tissue, such as meristematic tissue, with young rapidly growing shoots, leaves, roots and flower buds being preferred.

In the methods of the present invention, the plants or plant parts are preferably treated with an effective amount of an inhibitor or test compound. One of ordinary skill in the art would be able to determine the effective amount of any particular test compound by routine experimentation. For example, about a 1 $\mu$M to 1,000 $\mu$M, more preferably about 5 $\mu$M to 500 $\mu$M, most preferably about 10 $\mu$M to 100 $\mu$M solution of the test compound should be employed, depending on the potency. The solution containing the test compound may be combined with a 1 $\mu$M to 1,000 $\mu$M solution, preferably about 5 $\mu$M to 500 $\mu$M, most preferably about 10 $\mu$M to 100 $\mu$M, of the KARI inhibitor; and/or a 1 $\mu$M to 1,000 $\mu$M solution, preferably about 5 $\mu$M to 500 $\mu$M, most preferably about 10 $\mu$M to 100 $\mu$M, of the AHAS inhibitor. Of course higher concentrations would be similarly effective but may be wasteful and are usually not necessary.

The amount of AL and AHB present in the treated plants and plant parts may be determined according to known procedures in the art such as the method of Westerfeld (*J. Biol. Chem*, 161, 495–502 (1945)) or gas liquid chromatography.

To determine the amount of AL and AHB present in a plant or plant part according to the method of Westerfeld, the AL and AHB present in the plant or plant part is extracted into water; the water extract is treated with sulfuric acid; the acidified water extract solution is treated with a 0.5% creatine solution and a 5% a-naphthol in sodium hydroxide solution; and the color of the resulting solution is measured to determine the amount of AL and AHB present in the treated plant or plant part.

In order to facilitate a further understanding of the invention, the following examples are presented to illustrate more specific details thereof. The invention is not to be limited thereby as the full scope of the invention is defined in the claims.

EXAMPLE 1

Evaluation of In Vivo Inhibition of Acetohydroxyacid Synthase

Plant Material

Corn (*Zea mays*) (Pioneer var. 3475) and sunflower (*Helianthus annuus*) (Dahlgran var. DO-164) seeds are germinated and grown for 6 days in cylinders of germination paper that are kept moist by standing the cylinders in distilled water in a 1 L beaker covered with a perforated plastic bag. Seedlings are transferred to 120 mL plastic containers and grown hydroponically in a modified nutrient solution. All plants are grown in a growth chamber (13 h photoperiod; 28°/22° C.; 300 $\mu$E/m$^2$/sec). Corn is treated when the fourth leaf is just emerging from the whorl and sunflowers when the third leaf is emerging. Sulfonylurea-resistant and sensitive chickweed (*Stellaria media*) are grown from seed in the greenhouse until the plants reach the 2 to 4 leaf stage.

Treatments

Stock solutions of 10 $\mu$M technical (dimethylphosphinyl)glycolic acid are made by dissolving 1.52 mg/mL in water and are kept frozen until use. Solutions of different concentrations are made by dilution from this stock solution. Ten $\mu$M stock solutions of imazaquin and sulfometuron-methyl are made by dissolving 3.11 and 3.64 mg/mL of technical material, respectively, in a suitable organic solvent, such as acetone or tetrahydrofuran, and dilutions made from these stock solutions. Technical grade amino acids are dissolved directly in application solutions to the desired final concentrations.

In excised shoot (plant part) experiments, shoots are cut free from the roots under degassed water and the excised shoots are placed in vials containing the treatment solutions. At harvest, plants are weighed, cut up, and 1 or 2 g samples are frozen immediately in liquid nitrogen and kept in a −20° C. freezer until analysis.

In the experiment with sulfonylurea-resistant *Stellaria media*, plants are sprayed with one of the following treatments: 250 g/ha (dimethylphosphinyl)glycolic acid; 250 g/ha imazapyr; 10 g/ha chlorsulfuron; 250 g/ha (dimethylphosphinyl)glycolic acid plus 250 g/ha imazapyr; and 250 g/ha (dimethylphosphinyl)glycolic acid plus 20 g/ha chlorsulfuron; with a moving belt sprayer in a spray volume of 400 L/ha. Plants are kept in a greenhouse until the tissue is extracted to measure AL and AHB levels.

Extraction and Assay Procedures

Plant tissue is pulverized in liquid nitrogen with sand and then ground in ice cold 100 mM phosphate buffer, pH 7.5 (2 mL/g). The mixture is strained through several layers of cheesecloth into a 50 mL centrifuge tube, centrifuged at 24000 g for 15 minutes and the supernatant collected for analysis.

A portion of the supernatant is assayed directly for acetoin and another portion is acidified to 1% $H_2SO_4$ (v/v) and heated for 15 minutes at 60° C. to decarboxylate the AL and AHB. The resulting products are assayed using the method of Westerfeld and the combined product concentration is measured. There is no Westerfeld-positive product in untreated tissue based on differences between extracts before and after acidification. Because of this, the $OD_{520}$ of extracts from untreated tissue is used to correct for background color.

Results

Concentrations of (dimethylphosphinyl)glycolic acid above 1 $\mu M$ cause an accumulation of AL and AHB in excised corn shoots within 8 hours after application (Table I). Maximum levels appear to accumulate in plants treated with 10 $\mu M$ to 100 $\mu M$ solutions of (dimethylphosphinyl)glycolic acid. A time course of this accumulation in excised corn shoots shows that a maximum level is reached by 4 hours after application (Table II). This accumulation can be completely prevented by simultaneously treating the shoots with a 10 $\mu M$ solution of imazaquin. (Dimethylphosphinyl)glycolic acid causes an accumulation of AL and AHB in excised sunflower shoots which can be prevented by imazaquin treatment (Table III).

Other AHAS inhibitors such as sulfometuron-methyl in the presence of the amino acids valine and leucine (and isoleucine) also prevent the accumulation of AL and AHB caused by (dimethylphosphinyl)glycolic acid (Table IV).

The interaction between (dimethylphosphinyl)glycolic acid and AHAS inhibitors can also be used to determine if a plant is resistant to the AHAS inhibitors. (Dimethylphosphinyl)glycolic acid causes an accumulation of AL and AHB in chlorsulfuron-resistant *S. media*. The (dimethylphosphinyl)glycolic acid-induced accumulation of AL and AHB is prevented by imazapyr (Table V).

These results also indicate that this relatively easy method can be used to differentiate between AHAS inhibitor resistant and susceptible biotypes by treating plants with a combination of (dimethylphosphinyl)glycolic acid and different AHAS inhibitors. If the biotype is resistant to the AHAS inhibitor, then it will continue to accumulate AL and AHB in the presence of the inhibitor. These data also show that the interaction between AHAS and KARI inhibitors can be used to study the in vivo inhibition of AHAS by monitoring the buildup of AL and AHB in the plant tissue.

In Tables I-V, the AL/AHB levels are given in terms of the optical density reading at 520 nanometers ($OD_{520}$) per gram of fresh weight.

TABLE I

Effect of different concentrations of (dimethylphosphinyl)glycolic acid on AL and AHB accumulation in excised corn shoots eight hours after application

| Concentration of (Dimethylphosphinyl)-glycolic acid ($\mu M$) | AL/AHB Levels |
|---|---|
| 0.1 | 0.0 |
| 0.25 | 0.0 |
| 1 | 1.8 |
| 2.5 | 9.7 |
| 10 | 23.4 |
| 25 | 26.2 |
| 100 | 31.7 |

TABLE II

Time course of AL and AHB accumulation in excised corn shoots

| Treatment | Conc. ($\mu M$) | AL/AHB Levels Time after treatment (hours) | | | |
|---|---|---|---|---|---|
| | | 2 | 4 | 6 | 8 |
| (Dimethylphosphinyl)-glycolic acid | 100 | 6.9 | 9.7 | 14.2 | 14.7 |
| Imazaquin | 10 | 0 | 0 | 0 | 0 |
| Imazaquin + (Dimethylphosphinyl)-glycolic acid | 10 + 100 | 0 | 0 | 0 | 0 |

TABLE III

Effect of (dimethylphosphinyl)glycolic acid alone and in combination with imazaquin on AL and AHB accumulation in excised sunflower shoots

| Treatment | Conc. ($\mu M$) | AL/AHB Levels |
|---|---|---|
| Dimethylphosphinyl)-glycolic acid | 100 | 0.3 |
| (Dimethylphosphinyl)-glycolic acid + Imazaquin | 100 + 10 | 0.05 |

TABLE IV

Effect of (dimethylphosphinyl)glycolic acid and various AHAS inhibitors on accumulation of AL and AHB in excised corn shoots

| Treatment | Conc. ($\mu M$) | AL/AHB Levels |
|---|---|---|
| (Dimethylphosphinyl)glycolic acid | 100 | 18 |
| (Dimethylphosphinyl)glycolic acid + Valine + Leucine | 100 + 10 + 100 | 1 |
| (Dimethylphosphinyl)glycolic acid + Sulfometuron-methyl | 100 + 1 | 0 |

TABLE V

Effect of (dimethylphosphinyl)glycolic acid alone and in combination with various AHAS inhibitors on AL and AHB accumulation in chlorsulfuron resistant *S. media*

| Treatment | Rate (g/ha) | AL/AHB Levels Hours after treatment | |
|---|---|---|---|
| | | 24 | 48 |
| (Dimethylphosphinyl)glycolic acid | 250 | 25 | 53 |
| Chlorsulfuron | 10 | 0 | 0 |
| Imazapyr | 250 | 0 | 0 |
| (Dimethylphosphinyl)glycolic acid + Chlorsulfuron | 250 + 10 | 5 | 25 |

TABLE V-continued

Effect of (dimethylphosphinyl)glycolic acid alone and in combination with various AHAS inhibitors on AL and AHB accumulation in chlorsulfuron resistant *S. media*

| Treatment | Rate (g/ha) | AL/AHB Levels Hours after treatment | |
|---|---|---|---|
| | | 24 | 48 |
| (Dimethylphosphinyl)glycolic acid + Imazapyr | 250 + 250 | 0 | 0 |

EXAMPLE 2

Evaluation of In Vivo Inhibition of Acetohydroxyacid Synthase in Excised Lima Bean Shoots Young lima bean shoots with primary leaves that are approximately 30% expanded are excised and the cut stem is placed in a 5 μM imazaquin solution, a 100 μM (dimethylphosphinyl)glycolic acid solution, a 100 μM sodium N-hydroxy-N-isopropyloxamate solution, or a 5 μM imazaquin and 100 μM sodium N-hydroxy-N-isopropyloxamate solution. The excised shoots plus solutions are placed in a lighted growth chamber (28° C.) for 7 hours. After this incubation the primary leaves are harvested, frozen overnight at −20° C. and then extracted in boiling water and the level of AL and AHB measured in the water using the Westerfeld reaction.

As can be seen from the data in Table VI, sodium N-hydroxy-N-isopropyloxamate causes an accumulation of AL and AHB in excised lima bean shoots which can be prevented by imazaquin treatment.

In Table VI, the AL/AHB levels are reported in terms of the optical density reading at 520 nanometers (OD$_{520}$) per gram of fresh weight.

TABLE VI

Effect of sodium N-hydroxy-N-isopropyloxamate alone and in combination with imazaquin on AL and AHB accumulation in excised lima bean shoots

| Treatment | Conc. (μM) | AL/AHB Levels |
|---|---|---|
| Imazaquin | 5 | 0.0 |
| (Dimethylphosphinyl)glycolic acid | 100 | 16.6 |
| Sodium N-hydroxy-N-isopropyloxamate | 100 | 13.2 |
| Sodium N-hydroxy-N-isopropyloxamate + Imazaquin | 100 + 5 | 2.1 |

EXAMPLE 3

Evaluation of In Vivo Inhibition of Acetohydroxyacid Synthase in Susceptible and Heterozygous-resistant Tobacco Leaf discs (7 mm diameter) are cut from young expanding leaves of imazaquin susceptible and heterozygous-resistant tobacco (*Nicotiana tabacum*). Fifteen discs from each species are floated on 10 mL of a 5 μM imazaquin solution, a 100 μM (dimethylphosphinyl)glycolic acid solution, a 100 μM sodium N-hydroxy-N-isopropyloxamate solution, a 5 μM imazaquin and 100 μM (dimethylphosphinyl)glycolic acid solution, or a 5 μM imazaquin and 100 μM sodium N-hydroxy-N-isopropyloxamate solution contained in a petri plate. The discs plus solutions are incubated in a lighted growth chamber for 16 hours. Then the discs are harvested, frozen on dry ice and extracted in boiling water. The AL and AHB level in the water is determined using the Westerfeld reaction.

As can be seen from the data in Table VII, (dimethylphosphinyl)glycolic acid and sodium N-hydroxy-N-isopropyloxamate cause an accumulation of AL and AHB in tobacco leaf discs. This accumulation can be prevented in susceptible tobacco by imazaquin treatment. And AL and AHB accumulation in heterozygous-resistant tobacco can be prevented up to 50% by imazaquin treatment.

In Table VII, A designates imazaquin susceptible tobacco and B designates imazaquin heterozygous-resistant tobacco.

In Table VII, the AL/AHB levels are reported in terms of the optical density reading at 520 nanometers (OD$_{520}$) per gram of fresh weight.

TABLE VII

| Treatment | Conc. (μM) | AL/AHB Levels Tobacco Species | |
|---|---|---|---|
| | | A | B |
| Imazaquin | 5 | 0.0 | 0.0 |
| (Dimethylphosphinyl)glycolic acid | 100 | 2.7 | 2.2 |
| Sodium N-hydroxy-N-isopropyloxamate | 100 | 2.1 | 1.8 |
| (Dimethylphosphinyl)glycolic acid + Imazaquin | 100 + 5 | 0.0 | 1.2 |
| Sodium N-hydroxy-N-isopropyloxamate + Imazaquin | 100 + 5 | 0.2 | 1.0 |

EXAMPLE 4

Evaluation of In Vivo Inhibition of Acetohydroxyacid Synthase in Various Weed Species Samples of imazaquin susceptible crabgrass, morning glory and Johnsongrass and imazaquin resistant cocklebur are treated with a 0.2% imazaquin solution, a 0.1% (dimethylphosphinyl)glycolic acid solution or a 0.2% imazaquin and 0.1% (dimethylphosphinyl)glycolic acid solution. Approximately one gram of the material from each of the treatments is placed in a test tube and 5 mL of water is added. The test tubes with the leaf material plus water are heated in a boiling water bath for 15 minutes. Three to 150 μL aliquots of the water extract are placed in separate wells of a 96-well microtiter plate for each treatment. Twenty-five μL of 5% H$_2$SO$_4$ is added to each well and the plate is heated at 60° C. for 15 minutes. Seventy-five μL each of 0.5% creatine in water and 5% α-naphthol in 4N NaOH is added to each well and the plate is heated at 60° C. for 15 minutes. The plate is centrifuged for 10 minutes at 3000 g and the OD$_{520}$ is read for each well on a microtiter plate reader. The results are summarized in Table VIII.

As can be seen from the data in Table VIII, (dimethylphosphinyl)glycolic acid causes an accumulation of AL and AHB in various weed species. This accumulation can be prevented in crabgrass, morning glory and Johnsongrass by imazaquin treatment. The accumulation of AL and AHB in the cocklebur plant was reduced by one-half by imazaquin treatment. Therefore, these results indicate that the cocklebur plant is resistant to imazaquin.

In Table VIII, the acetolactate and acetohydroxybutyrate levels are reported in terms of the optical density reading at 520 nanometers (OD$_{520}$) per gram of fresh weight.

TABLE VIII

| Treatment | Acetolactate/Acetohydroxybutyrate Levels Weed Species | | | |
|---|---|---|---|---|
| | Crab-grass | Morning glory | Johnson-grass | Cocklebur |
| Imazaquin | 0 | 0 | 0 | 0 |
| (Dimethyl-phosphinyl)glycolic acid | 1.7 | 1.5 | 0.5 | 1.0 |
| (Dimethyl-phosphinyl)glycolic acid + Imazaquin | 0 | 0 | 0 | 0.5 |

EXAMPLE 5

Evaluation of In Vivo Inhibition of Acetohydroxyacid Synthase in Imazaquin Susceptible and Resistant Cocklebur (*Xanthium Strumarium*)

Imazaquin susceptible and resistant cocklebur plants are treated in the field with a 0.1% imazaquin solution, a 0.1% (dimethylphosphinyl)glycolic acid solution or a 0.1% imazaquin and 0.1% (dimethylphosphinyl)-glycolic acid solution. One or two days after treatment, the young rapidly expanding leaves are collected. Approximately one gram of the leaf material from each of the treatments is placed in a test tube and 5 mL of water is added. The test tubes with the leaf material plus water are heated in a boiling water bath for 15 minutes. Three to 150 µL aliquots of the water extract are placed in separate wells of a 96-well microtiter plate for each treatment. Twenty-five µL of 5% $H_2SO_4$ is added to each well and the plate is heated at 60° C. for 15 minutes. Seventy-five µL each of 0.5% creatine in water and 5% α-naphthol in 4N NaOH is added to each well and the plate is heated at 60° C. for 15 minutes. The plate is centrifuged for 10 minutes at 3000 g and the $OD_{520}$ is read for each well on a microtiter plate reader. The results are summarized in Table IX.

As can be seen from the data in Table IX, (dimethylphosphinyl)glycolic acid causes an accumulation of AL and AHB in both cocklebur plants. This accumulation can be prevented in the imazaquin susceptible cocklebur plant. However, the accumulation of AL and AHB in the other cocklebur plant could not be completely prevented by imazaquin treatment. Therefore, these results indicate that this cocklebur plant is resistant to imazaquin.

TABLE I

| Treatment | AL/AHB Levels Cocklebur Plant | |
|---|---|---|
| | Imazaquin-Susceptible | -Resistant |
| (Dimethylphosphinyl)-glycolic acid | 3.42 | 3.44 |
| (Dimethylphosphinyl)-glycolic acid + Imazaquin | 0.04 | 1.39 |

I claim:

1. An in vivo method for determining whether a compound inhibits acetohydroxyacid synthase which comprises:
    (a) treating a first acetohydroxyacid synthase inhibitor-susceptible plant or plant part with an effective amount of the compound and an effective amount of a ketol-acid reductoisomerase inhibitor;
    (b) treating a second acetohydroxyacid synthase inhibitor-susceptible plant or plant part from the same population of the same species with the effective amount of the ketol-acid reductiosomerase inhibitor alone; and
    (c) measuring the amounts of acetolactate and acetohydroxybutyrate present in the treated plants or plant parts to determine if the amount of acetolactate and acetohydroxybutyrate present in (a) is less than the amount of acetolactate and acetohydroxybutyrate present in (b).

2. The method according to claim 1 wherein the ketol-acid reductoisomerase inhibitor is selected from the group consisting of (dimethylphosphinyl)glycolic acid, 2-(dimethylphosphinoyl)-2-hydroxyacetic acid, sodium N-hydroxy-N-alkyloxamate and sodium N-hydroxy-N-aralkyloxamate.

3. The method according to claim 2 wherein the alkyl component of the N-hydroxy-N-alkyloxamate is selected from $C_1$–$C_6$ alkyl and $C_3$–$C_7$ cycloalkyl.

4. The method according to claim 3 wherein the alkyl component is isopropyl.

5. The method according to claim 2 wherein the aralkyl component is benzyl.

6. The method according to claim 1 wherein the acetohydroxyacid synthase inhibitor susceptible plant is selected from the group consisting of a monocotyledonous plant and a dicotyledonous plant.

7. The method according to claim 1 wherein the plant parts are young rapidly growing tissue.

8. The method according to claim 1 wherein the amount of acetolactate and acetohydroxybutyrate present in the treated plant or plant part is determined by:
    (a) extracting the acetolactate and acetohydroxybutyrate present in the treated plant or plant part into water;
    (b) treating the water extract with a sulfuric acid solution;
    (c) treating the acidified water extract solution from (b) with a 0.5% creatine solution and a 5% α-naphthol in sodium hydroxide solution; and
    (d) measuring and comparing the color of the product of (c) to a known standard.

9. The method according to claim 1 wherein the plant or plant part is treated with a 1 µM to 1,000 µM solution of the compound and a 1 µM to 1,000 µM solution of the ketol-acid reductoisomerase inhibitor.

10. An in vivo method for determining whether a population of a plant species is resistant to an acetohydroxyacid synthase inhibitor which comprises:
    (a) treating a first plant or a part of the plant with an effective amount of the acetohydroxyacid synthase inhibitor and an effective amount of a ketol-acid reductoisomerase inhibitor;
    (b) treating a second plant or plant part from the same population of the same species with the effective amount of the ketol-acid reductoisomerase inhibitor alone;
    (c) measuring the amounts of acetolactate and acetohydroxybutyrate present in the treated plants or plant parts to determine if the amount of acetolactate and acetohydroxybutyrate present in (a) is at least about 15% of the amount of acetolactate and acetohydroxybutyrate present in (b).

11. The method according to claim 10 wherein the acetohydroxyacid synthase inhibitor is selected from the group consisting of an imidazolinone, a sulfonylurea, a sulfonamide and a pyrimidyloxybenzoate.

12. The method according to claim 11 wherein the imidazolinone is selected from the group consisting of 5-ethyl-2-(4-isopropyl-4-methyl-5-oxo-2-imidazolin-2-yl)nicotinic acid;

2-(4-isopropyl-4-methyl-5-oxo-2-imidazolin-2-yl)-3-quinolinecarboxylic acid;

isopropylammonium 2-(4-isopropyl-4-methyl-5-oxo-2-imidazolin-2-yl)nicotinate;

methyl 2-(4-isopropyl-4-methyl-5-oxo-2-imidazolin-2-yl)nicotinate; and 2-(4-isopropyl-4-methyl-5-oxo-2-imidazolin-2-yl)-5-methylnicotinic acid.

13. The method according to claim 10 wherein the ketol-acid reductoisomerase inhibitor is selected from the group consisting of (dimethylphosphinyl)glycolic acid, 2-(dimethylphosphinoyl)-2-hydroxyacetic acid, sodium N-hydroxy-N-alkyloxamate and sodium N-hydroxy-N-aralkyloxamate.

14. The method according to claim 13 wherein the alkyl component of the N-hydroxy-N-alkyloxamate is selected from $C_1$–$C_6$ alkyl and $C_3$–$C_7$ cycloalkyl.

15. The method according to claim 14 wherein the alkyl component is isopropyl.

16. The method according to claim 13 wherein the aralkyl component is benzyl.

17. The method according to claim 10 wherein the plant parts are young rapidly growing tissue.

18. The method according to claim 10 wherein the amount of acetolactate and acetohydroxybutyrate present in the treated plant or plant part is determined by
 (a) extracting the acetolactate and acetohydroxybutyrate present in the plant or plant part into water;
 (b) treating the water extract with a sulfuric acid solution;
 (c) treating the acidified water extract solution from (b) with a 0.5% creatine solution and a 5% α-naphthol in sodium hydroxide solution; and
 (d) measuring and comparing the color of the product of (c) to a known standard.

19. The method according to claim 10 wherein the plant or plant part is treated with a 1 μM to 1,000 μM solution of the acetohydroxyacid synthase inhibitor and a 1 μM to 1,000 μM solution of the ketol-acid reductoisomerase inhibitor.

* * * * *